United States Patent [19]

Kubo et al.

[11] Patent Number: 5,419,895
[45] Date of Patent: May 30, 1995

[54] COMPOSITION FOR TREATING HUMAN HAIR AND METHOD OF USE

[75] Inventors: Sanae Kubo, Sagamihara; Tomiyuki Nanba; Toshihiko Nakane, both of Yokohama, all of Japan

[73] Assignee: Shiseido Co., Ltd., Tokyo, Japan

[21] Appl. No.: 921,350

[22] Filed: Jul. 29, 1992

[30] Foreign Application Priority Data

Aug. 2, 1991 [JP] Japan .................. 3-216413

[51] Int. Cl.$^6$ .................. A61K 7/09; A61K 7/06
[52] U.S. Cl. .................. 424/70.51; 424/70.5; 424/70.1; 132/204; 132/208
[58] Field of Search .............. 424/71, 72, 70; 564/500, 511

[56] References Cited

U.S. PATENT DOCUMENTS

| 2,540,494 | 2/1951 | Schwarz | 424/72 |
| 2,719,813 | 10/1955 | Haekle | 424/71 |
| 2,751,409 | 5/1956 | Kuhn | 424/71 |
| 3,312,732 | 4/1967 | Gollis | 564/500 |
| 4,504,466 | 3/1985 | Eda | 424/72 |
| 4,621,098 | 11/1986 | Umminger | 514/706 |
| 4,816,246 | 3/1989 | Matthews | 424/72 |
| 5,165,427 | 11/1992 | Borish | 424/71 |

OTHER PUBLICATIONS

Mitsui Toatsu Chem Inc. JA 0140760 (31 Aug. 1982).

Primary Examiner—Thurman K. Page
Assistant Examiner—Sally Gardner
Attorney, Agent, or Firm—Townsend & Banta

[57] ABSTRACT

A composition for treating hair comprised of a thiol compound that is a superior hair reductant and hair cosmetic, especially in terms of waving effect, odor, hair damage, texture and safety and where the thiol compound has the formula $HS-(CH_2)_n-NH-(CH_2)_m-NH_2$ and the n and the m are integers from 1 to 4. The composition may include the salts of the compound. The composition is useful for a method of treating hair by applying the composition to the hair; leaving the composition on the hair for a sufficient period of time, depending on the desired effect; and then removing the composition. The invention, in particular, relates to hair reductants as well as primary agents for permanent waving, pretreatment agents for hair dyeing, cosmetics for heated hair curling, cosmetics for frizzy hair and cosmetics for human hair removing.

1 Claim, No Drawings

COMPOSITION FOR TREATING HUMAN HAIR AND METHOD OF USE

BACKGROUND OF THE INVENTION

1. Field of the Invention

The present invention relates to a composition for treating human hair comprised of a thiol compound that is a superior hair reductant and hair cosmetic especially in terms of waving effect, odor, hair damage, texture and safety.

The present invention also relates to a method of treating human hair using this composition.

2. The Prior Art

Hair reductants currently used in Japan are ammonium thioglycolate calciumthioglylate and cysteine.

Of these, primary agents for permanent waving (hereafter referred to as "primary agents for permanents") which contain ammonium thioglycolate have the characteristic of giving a strong wave effect.

However, these primary agents for permanents have the following shortcomings:

1. The degree of hair damage is high and the hair texture tends to deteriorate.
2. Skin irritation may result if the manner of preparation or use of the liquid agents are improper.
3. There is an offensive odor characteristic of permanent agents which is caused by the thioglycolic acid.

Although much effort has been put towards solving these shortcomings, currently they have not been solved.

On the other hand, it is believed that primary agents for permanents which contain cystsine cause less hair damage and in general cause less skin irritation and have a less offensive odor at room temperature.

However, these primary agents for permanents have the following shortcomings:

1. The waving effect is weak. Since the waving effect is weak, a means such as strengthening the alkalinity with liquid agent formulas is likely to be used, resulting in possible skin irritation caused by alkalinity.
2. Cysteine is not stable, so that when the liquid agent is old or exposed to high temperatures the cystsine content decreases and, at the same time, a considerable amount of hydrogen sulfide is generated as a byproduct, resulting in the offensive odor problem characteristic of permanents.

Currently, these shortcomings have not yet been overcome. Recently, another type of hair cosmetics, those which contain sulfides and such as hair reductants, have begun to be commercially sold.

Their features include very little of the offensive odor characteristic of permanents and a high degree of safety against hair damage and skin irritation.

However, these hair reductants have the following serious problems:

1. Since their reducing action on the hair is so weak, the heated hair curling cosmetics, for example, used by heating up to 60° C. or less, require prolonged heat treatment because of the weak curling. Also, in the case of cosmetics for frizzy hair and cosmetics for hair softening, a one-time treatment hardly produces an effect and thus on-going use is required.

By the way, Calcium thioglycollate is a reducing agent for human hair which is currently used in Japan as a hair remover for the removal of unwanted hair (body hair) from arms and legs.

A hair remover containing calcium thioglycollate softens and removes unwanted hair (body hair) from arms and legs. However, it has the following shortcomings.

(1) Since the hair remover must have a strongly alkaline pH of 11-12, it is very hard on skin of arms and legs. If the recipe or usage is not appropriate, it may lead to skin irritation and thus cause problems.

(2) The characteristic offensive odor arising from thioglycollic acid is not desirable.

Also, in general, since an acidic hair dye has a weak dyeing power particularly on healthy gray hair, it is known: that treating the hair with an alkaline solution such as ammonium thioglycollate and cysteine before the acidic hair dye treatment improves the dyeing result somewhat. However, there are problems as follows:

(1) The characteristic offensive odor arising from thioglycollic acid is not desirable, and (2) Since the pretreatment before dyeing is conducted at an alkaline pH and the acidic hair dye is acidic, efficiency is low.

In this current situation, the inventor wholeheartedly searched for and evaluated various new reductants. As a result, we have found hair reductants which are superior to conventional thioglycolate and cysteine in terms of waving effect, hair-removing effect, improving of dyeing effect, odor, hair damage, texture, safety, etc.

SUMMARY OF THE INVENTION

The object of the present invention is to provide a composition for treating hair comprised of a thiol compound that is a superior human hair reductant and hair cosmetic, especially in terms of waving effect, odor, hair damage, texture and safety and where the thiol compound has the formula HS—(CH2)n—NH(CH2-)m—NH2 and the n and m are integers from 1 to 4, The composition may include the salts of the compound.

The present invention further relates to a method of treating hair by applying the composition to the hair; leaving the composition on the hair for a sufficient period of time, depending on the desired effect; and then removing the composition.

The present invention provides hair reductants and hair cosmetics which are superior to conventional thioglycolate and cysteine in terms of waving effect, hair-removing effect, improving of dyeing effect odor, hair damage, texture, safety, etc.

At the same time, we have found many advantages to using this composition as a hair reductant in combination with conventional hair reductants, and thus completed this invention.

This composition as a hair reductant in combination with conventional hair reductants also provides a hair reductant of the invention that is superior to conventional thioglycolates and cysteine in terms of waving effect and texture, and as good as conventional thioglycolates and cysteine in terms of hair damage and odor.

The first point of this invention concerns hair reductants which are characteristically composed of thiol compounds or their salts, whose chemical composition is formulated by,

HS—(CH2)n—NH—(CH2) m-NH2　　　(Formula 1)

wherein n and m are integers from 1 to 4.

The second point of this invention concerns hair cosmetics which characteristically contain the thiol compounds or their salts, whose chemical composition is formulated by Formula 1, as a reductant.

The third point of this invention concerns hair cosmetics which characteristically contain the thiol compounds or their salts, whose chemical composition is formulated by Formula I, as well as one or more of the following compounds: thioglycolic acid, thiolactic acid, cysteine, homocysteine, N-acetylcysteine, cysteamine, N-acetylcysteamine, thiomalic acid, glycerolmonothioglycolate, thioglycerine and their salts, sulfites, hydrogensulfites, pyrosulfites and thiosulfates.

The fourth point of this invention concerns primary agents for permanent waving, pretreatment agents for hair dyeing, cosmetics for heated-type hair curling, cosmetics for hair softening or cosmetics for frizzy hair which characteristically contain the thiol compounds or their salts, whose chemical composition is formulated by Formula 1, as a reductant.

The fifth point of this invention concerns primary agents for permanent waving, pretreatment agents for hair dyeing, cosmetics for heated-type hair curling, cosmetics for hair softening, cosmetics for frizzy hair or cosmetics for human hair remover which characteristically contain the thiol compounds or their salts, whose chemical composition is formulated by Formula 1, as well as one or more of the following compounds: thioglycolic acid, thiolactic acid, cysteine, homocysteine, N-acetylcysteine, cysteamine, N-acetylcysteamine, thiomalic acid, glycerolmonothioglycolate, thioglycerine and their salts, sulfides, hydrogensulfites, pyrosulfides and thiosulfates.

DETAILED DESCRIPTION OF THE PREFERRED EMBODIMENTS

The composition for treating hair of the present invention either solely contains the thiol compounds or their salts formulated by Formula 1, or contain them together with other reductants. If it contains only the thiol compounds or their salts, then hair cosmetics which are superior to conventional cosmetics in terms of waving effect, odor, hair damage, texture, safety, etc., are obtained. If it contains other reductants as well, then hair cosmetics which are superior to conventional cosmetics in terms of waving effect and texture, and as good as conventional cosmetics in terms of hair damage and such are obtained.

The hair reductants from the present invention are composed of thiol compounds or their salts formulated by Formula 1. While n and m are integers from preferable if n=2 and m=2 or 3.

Examples of the hair cosmetics of this invention include primary agents for permanent waving, pretreatment agents for hair dyeing, cosmetics for heated-type hair curling, cosmetics for hair softening and cosmetics for frizzy hair.

The primary agents for permanent waving can be used as primary agents for the cold two-bath type, heated two bath type and prepared-at-use exoergic type waves, and also as primary agents for curly hair straightening agents.

Blending Ratio

When blending the thiol compounds or their salts formulated by Formula 1 into hair cosmetics, the blending ratio can be freely changed according to the target efficacy and effect of the hair cosmetics. For example, when they are blended as primary agents for permanents, 1.0 to 50% (weight %) is preferable, and 2.0 to 20 % (weight %) is more preferable.

When used together with other reductants, while the weight ratio {reductants of Formula I or their salts} /{other reductants} can be any value, the weight ratio {reductants of Formula 1 or their salts}/{other reductants} should preferably be 0.05 or more in order to take advantage of combined use, The preferable upper limit is 100, above which the effect becomes the same as when only the reductants of Formula 1 are used.

When blending the thiol compounds or their salts formulated by Formula 1 into hair cosmetics such as heated-type hair curling agents, cosmetics for hair softening, cosmetics for frizzy hair or pretreatment agents for hair dyeing, it is normally preferable to have a lower blending ratio compared to when they are blended as primary agents for permanents, and more specifically 2.0% (weight %) or less is preferable.

Also in this case, when used together with other reductants, the weight ratio {reductants of Formula 1 or their salts}/{other reductants}should preferably be 0.05 or more. When blending the thiol compounds formulated in Formula 1 into cosmetics, it is normally preferable to have them in salt form as formulated by the following Formula 2,

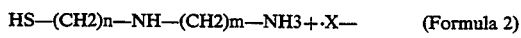

HS—(CH2)n—NH—(CH2)m—NH3+·X— (Formula 2)

wherein n and m are the same as in the general formula (1). X— is the an ion part of an inorganic acid such as hydrochloric acid, sulfuric acid, phosphoricacid or carbonic acid, or of an organic acid such as ethylsulfuric acid, methylsulfuric acid, citric acid, acetic acid, tartaric acid, oxalic acid, lactic acid or acidic aminoacids, As the alkali agent used to make the hair cosmetics, to which the thiol compounds or their salts formulated in Formula 1 are blended, have an alkaline pH, various alkali agents can be used. For example, aqueous ammonia, ammoniumcarbonate, ammonium hydrogencarbonate, monoethanolamine, diethanolamine, morpholine, triethanolamine, aminomethylpropanol, aminomethylpropanediol, isopropanolamine, guanidine, guanidine chloride, guanidine carbonate, guanidinesulfate, L-arginine, L-lysine and inorganic alkali agents can be used. The pH of the cosmetics is preferably 3 to 11, and more preferably 7.5 to 10.

Other Additives

In addition to those mentioned above, there are various useful additives which can be blended into hair cosmetics.

For example: urea, alkylurea, taurine, hydantoin, hydantoic acid, lithium halogenares, various solvents and polyvalent-ols as effect accelerators; various anionic, ampholytic, cationic and nonionic surfactants as penetration assistants and wetting accelerators; various peptides, oligopeptides, polypeptides and proteins, mink oil, lanolin and hydrocarbon oils as hair protectors; silicone derivatives such as emulsion formulations of silicone and amodimethicone, cation modified silicone, bunte modified silicone, glycol modified silicone and trimethylcyritates of amino modified silicone, as well as various cationic polymers as hair texture improvement agents; scent agents; sequestering agents; coloring agents, etc., can be blended.

In a case of a hair remover: the skin irritation relievers include glycerine, 1-3 butyleneglycol, sorbitol, hexyleneglycol, propyleneglycol, dipropyleneglycol, diglycerine and polyglycerine; the skin emollient agents include various plant oils, animal oils, mineral oils, silicone and various silicone derivatives, higher alcohols, higher fatic acids and emulsifiers. It may contain various water soluble polymers, inorganic polymer perfume agents, sequestering agents, antiseptics and coloring to improve usability.

Also in a case of a hair dye: the solvents include benzylalcohol, N-methyl pyrolidone, ethylalcohol, isopropylalcohol, n-butylalcohol and phenylethylalcohol; the acids include organic acids such as citric acid, acetic acid, lactic acid, tartaric acid and acidic amino acids, as well as various inorganic acids; the acidic dyes include various tar dyes and natural dyes which dissolve in the solvents mentioned above or in water.

As far as the type of agent for these cosmetics is concerned, it is obviously possible to choose, according to the intended use, such types as a transparent liquid type, an emulsion/viscous emulsion type, a transparent gel type, a cream type, or a foamy aerosol or spray type.

EXAMPLE 1

We prepared primary agents for cold two bath type permanents with the compositions shown in Table 1, and evaluated the waving effect, hair damage, texture and odor.

Each evaluation was performed according to the following method:

Waving Effect

A hair bundle (12 hairs, 130 mm long) was uniformly wrapped around a glass rod (diameter 7 mm), immersed in the primary agent for permanents for 10 minutes at 30° C., and rinsed for 1 minute.

It was then immersed in a secondary permanent agent (6.0% NaBrO3, phosphate buffer, pH 5.5) for 10 minutes at 30° C., rinsed, and thus prepared as a hair coil.

The hair coil diameter and hair coil length of the hair coil thus prepared were measured. For both hair coil diameter and hair coil length, smaller values indicate a stronger waving effect.

Hair Damage

Permanent treatment, under the same treatment conditions as when the waving effect was measured, was conducted on a hair bundle (12 hairs, 60 mm long), and the hair strength ratio of before and after the permanent treatment was measured. Hair strength ratio values closer to 1.000 indicate less hair damage.

Odor

After preparation of the primary agents for permanents they were let stand for a week at room temperature and at 40° C., and then odor was evaluated by smelling (sense). Evaluation is indicated as follows:

⊚: No odor
Δ: Minor odor
X: Strong offensive odor
XX: Very strong offensive odor Texture after Permanent The texture after permanent was evaluated by touch (sense) after permanent treatment was conducted on 5 female panelers. The permanent treatment conditions were the same as for the waving effect measurement. Evaluation is indicated as follows:

⊚: Very good
○: Good
X: Poor

The results of the above-described evaluations are shown in Table 1 and Table 2.

In the tables, a value in parentheses () indicates the concentration (ppm) of hydrogen sulfide in 5 milliliters of the primary agent for permanents when it is discharged into 100 milliliters air volume.

TABLE 1

| Composition (w %) | Example (No. 1) | Example (No. 2) | Control (No. 3) | Control (No. 4) |
|---|---|---|---|---|
| Reductant | | | | |
| HS—CH2CH2—NH—CH2CH2—NH3.Cl | 10.22 | | | |
| HS—CH2CH2—NH—CH2CH2CH2—NH3.Cl | | 11.13 | | |
| Aqueous ammonium thioglycolate (50%) | | | 12.00 | |
| DL.cysteine.HCl.H2O | | | | 11.45 |
| Ethylenediaminetetraacetic acid-4 sodium | 0.1 | 0.1 | 0.1 | 0.1 |
| Polyoxyethylene (20 E.O.) cetylether | 0.1 | 0.1 | 0.1 | 0.1 |
| Monoethanolamine | Suitable amount | Suitable amount | Suitable amount | Suitable amount |
| Purified water | Balance | Balance | Balance | Balance |
| Total | 100 | 100 | 100 | 100 |

For each primary agent preparation, the pH at 25° C. was 8.5 ± 0.1, and the reductant level was 0.652N.

TABLE 2

| Evaluation | (Item) | Example (No. 1) | Example (No. 2) | Control (No. 3) | Control (No. 4) |
|---|---|---|---|---|---|
| Wave effect (mm) | Hair coil diameter | 9.5 | 10.3 | 17.3 | 26.2 |
| | Hair coil length | 19.7 | 23.6 | 40.8 | 55.4 |
| Hair damage | Hair strength ratio | 0.875 | 0.888 | 0.754 | 0.912 |
| Texture after permanent | Touch (sense) | ⊚ Very good | ⊚ Very good | X Poor | ○ Good |
| Odor of primary agent for permanents (Smelling:sense) | Let stand for 1 week at room temperature | ⊚ (0) | ⊚ (0) | X (416) | Δ (73) |
| | Let stand for 1 week at 40° C. | ⊚ (0) | ⊚ (0) | XX (830) | XX (1650) |

The comparison shows that Examples No. 1 and No. 2 are superior to Controls No. 3 (containing ammonium thioglycolate) and No. 4 (containing cysteine) in terms of waving effect, texture and odor.

It is also shown that they are superior to the Control (No. 3) in terms of hair damage, as well.

According to the 12-hour open patch test on 5 panelers, faint red spots were observed on two panelers in Control No. 3, but no faint red spots nor any other irritations were observed on any of the panelers in the examples.

EXAMPLE 2

We prepared primary agents for cold two bath type permanents with the compositions shown in Table 3, and evaluated the waving effect, hair damage and texture.

This embodiment shows examples in which other reductants as well as the thiol compounds formulated in Formula 1 contained. The results of the measurements are shown in Table 4.

TABLE 3

| Composition (w %) | Example (No. 5) | Example (No. 6) | Control (No. 7) | Control (No. 8) |
|---|---|---|---|---|
| Reductant | | | | |
| HS—CH2CH2—NH—CH2CH2—NH3.Cl | 2.0 | 2.0 | | |
| Aqueous ammonium thioglycolate (50%) | 10.0 | | 14.0 | |
| DL-cysteine | | 5.0 | | 6.5 |
| Ethylenediaminetetraacetic acid-4 sodium | 0.1 | 0.1 | 0.1 | 0.1 |
| Polyoxyethylene (20 E.O.) cetylether | 0.1 | 0.1 | 0.1 | 0.1 |
| Monoethanolamine | Suitable amount | Suitable amount | Suitable amount | Suitable amount |
| Purified water | Balance | Balance | Balance | Balance |
| Total | 100 | 100 | 100 | 100 |

For each primary agent preparation, the pH at 25° C. was 8.5 ± 0.1. Reductant: 7.0 W/W %

TABLE 4

| Evaluation | (Item) | Example (No. 5) | Example (No. 6) | Control (No. 7) | Control (No. 8) |
|---|---|---|---|---|---|
| Wave effect (mm) | Hair coil diameter | 9.8 | 10.9 | 12.8 | 28.4 |
| | Hair coil length | 23.5 | 27.8 | 36.3 | 63.9 |
| Hair damage | Hair strength ratio | 0.899 | 0.891 | 0.701 | 0.955 |
| Texture after permanent | Touch (sense) | ◉ | ◉ | X | ○ |

The methods for evaluating waving effect and hair damage for all but the hair used were the same as for Example 1.

In terms of waving effect and texture after permanent, it is shown that Example No. 5 is superior to Control No. 7, and Example No. 6 is superior to Control No. 8.

In terms of hair damage, Example No. 5 is superior to Control No. 7, and both Example No. 6 and Control No. 8 show good results.

EXAMPLE 3

We prepared cosmetics for heated-type hair curling with the compositions shown in Table 5, and evaluated the curling effect, hair damage and texture, The results are also shown in Table 5.

TABLE 5

| Composition (w %) | Example (No. 9) | Control (No. 10) |
|---|---|---|
| Reductant | | |
| HS—CH2CH2—NH—CH2CH2—NH3.Cl | 1.0 | |
| Sodium pyrosulfite | 4.0 | 4.0 |
| Ethylenediaminetetraacetic acid-4 sodium | 0.1 | 0.1 |
| Polyoxyethylene (20 E.O.) cetylether | 0.1 | 0.1 |
| Monoethanolamine | Suitable amount | Suitable amount |
| Purified water | Balance | Balance |
| Total | 100 | 100 |
| Evaluation Results | | |
| Curling effect (mm)   Hair coil diameter | 10.0 | 24.0 |
|                        Hair coil length | 30.2 | 66.6 |
| Hair damage   Hair strength ratio | 0.953 | 0.960 |
| Texture      Touch (sense) | ◉ | ◉ |

The curling agents were prepared to have a pH of 8.5 at 25° C. The evaluation method was almost the same as for Examplem 1, except that the curling agent treatment was conducted for 20 minutes at 40° C.

It is shown that Example No. 9 has a degree of texture and hair damage equivalent to Control No. 10, but that it is superior to Control No. 10 in terms of curling effect.

EXAMPLE 4

We prepared cold two bath type permanent agents with the following compositions:

| | (w %) |
|---|---|
| Primary agent for permanents | |
| 1. HS—CH2CH2—NH—CH2CH2—NH3.Cl | 6.0 |
| 2. Aqueous ammonium thioglycolate (50%) | 2.0 |
| 3. Monoethanolamine | 1.5 |
| 4. Ammonium hydrogen-carbonate | 2.5 |
| 5. L-arginine | 0.5 |
| 6. Amodimethicone emulsion* | 2.0 |
| 7. Stearyl-trimethyl ammonium chloride | 0.1 |
| 8. Polyoxyethylene (20 E.O.) cetylether | 0.5 |
| 9. Keratin hydrolysis product** | 1.0 |
| 10. Perfume | 0.1 |
| 11. Ethylenediaminetetraacetic acid 4-sodium | 0.1 |
| 12. Purified water | 83.7 |

-continued

| | (w %) |
|---|---|
| Secondary agent for permanents | |
| 1. Sodium bromate | 6.0 |
| 2. Purified water | 94.0 |

*Toray Silicone SM8702C, manufactured by Toray Dow-Corning Silicone, Ltd.
**Promois WK-H, manufactured by Seiwa Supply, Ltd.

Using 80 ml of the primary agent for permanents and 100 ml of the secondary agent for permanents, treatment with conventional methods was performed on women with medium length hair. Very resilient waves were obtained without a residual odor after the permanents, and smooth and shiny hair styles resulted.

EXAMPLE 5

We prepared a hair cosmetic for frizzy hair with the following composition:

| | (w %) |
|---|---|
| 1. HS—CH2CH2—NH—CH2CH2—NH3.Cl | 2.0 |
| 2. Sodium pyrosulfite | 5.0 |
| 3. Merquat 100*** | 1.0 |
| 4. Monoethanolamine | Suitable amount |
| 5. Aqueous ammonia (guaranteed reagent) | 2.0 |
| 6. Cetanol | 1.0 |
| 7. Stearyl-trimethyl ammonium chloride | 0.2 |
| 8. Polyoxyethylene (20 E.O.) cetylether | 0.1 |
| 9. Perfume | 0.1 |
| 10. Purified water | Balance |
| Total | 100.0% (w %) |

The pH was adjusted to 8.5 using monoethanolamine.
***A cation polymer manufactured by Merck, Ltd.

Using 80 ml of this liquid agent, heating with a hair dryer was conducted with a conventional method for 20 minutes at 50° C. The rods were then removed after adequate rinsing, resulting in resilient curls with good hair texture.

After shampooing in a bath tub, 10 ml of this liquid agent was applied, then rinsed off after letting stand for approximately 5 minutes. After repeating this treatment for approximately a week, the relatively stiff and somewhat frizzy hair of the woman became easier to manage, and soft and flowing.

EXAMPLE 6

We prepared a pretreatment agent for hair dyeing with the following composition:

| | (w %) |
|---|---|
| 1. HS—CH2CH2—NH—CH2CH2—NH3.Cl | 1.0 |
| 2. N-acetyl-L-cysteine | 1.0 |
| 3. Sodium carbonate | Suitable amount (pH 8.0) |
| 4. Polyoxyethylene (20 E.O.) cetylether | 0.1 |
| 5. Purified water | Balance |
| Total | 100.0 W % |

This agent was applied to the approximately 50% gray hair (side) of a male by using absorbent cotton soaked with approximately 5 ml of the agent, and the hair was let stand for 10 minutes. Then, after cleaning with a wet towel the area where this agent was applied, a commercial hair dyeing agent was applied, and the hair was let stand for 10 minutes. After rinsing and drying, the gray hair was nicely dyed and substantially less prominent. The effect was found to continue for approximately 2 weeks.

EXAMPLE 7

A hair dye with the following composition was prepared:

| | |
|---|---|
| 1. HS—CH2CH2—NH—CH2CH2—NH3.Cl | 1.0 |
| 2. Erythrocin (Red No. 3) | 0.1 |
| 3. Indigo carmine (Blue No. 2) | 0.1 |
| 4. Quinoline yellow WS (Yellow No. 203) | 0.1 |
| 5. Benzyl alcohol | 10.0 |
| 6. Ethyl alcohol | 10.0 |
| 7. Citric acid | 1.0 |
| 8. Xanthenegum | 1.0 |
| 9. Purified water | Balance |
| Total | 100% |

Approximately 80 ml of this agent was applied on the entire head of hair of a man with 50% gray hair. After letting stand for 10 minutes, the agent was thoroughly rinsed off with water. The hair was then washed with normal shampoo, wiped with a towel, and dried with a hair drier.

The gray hair became significantly less conspicuous, and the entire head of hair changed to natural looking black hair. The color held for approximately 2 weeks.

EXAMPLE 8

A hair remover cream with the following composition was prepared:

| | |
|---|---|
| 1. HS—CH2CH2—NH—CH2CH2—NH3.Cl | 1.0 |
| 2. Sodium hydroxide | Appropriate quantity (pH 10) |
| 3. Stearyl alcohol | 3.0 |
| 4. Cetyl alcohol | 3.0 |
| 5. Vaseline | 15.0 |
| 6. Liquid paraffin | 10.0 |
| 7. Polyoxyethylene (50 EO) oleyl other | 4.0 |
| 8. Polyoxyethylene (8 EO) oleyl ether | 1.7 |
| 9. Urea | 2.0 |
| 10. Perfume | Appropriate quantity |
| 11. Purified water | Balance |
| Total | 100.0 (Wt %) |

Approximately 10 g of this product was uniformly applied on a portion (10 cm×4 cm) of an arm with unwanted hair (body hair) and, after letting stand for 5 minutes, the area was thoroughly rinsed with warm water and wiped with a towel to remove excess moisture. The unwanted hair was removed clean. There was no skin irritation nor redness observed during or after use.

The composition of the invention for hair reductants can be contained in hair cosmetics. When contained alone, superior results are obtained compared to conventional cosmetics in terms of waving effect, odor, hair damage, texture and safety.

When contained together with other reductants, superior results are obtained compared to conventional cosmetics in terms of waving effect and texture, and equivalent results are obtained compared to conventional cosmetics in terms of hair damage and such. When the cosmetics are heated-type hair curling cosmetics, the curling effect is much superior to that of conventional cosmetics while hair damage and texture results are more or less equivalent.

When the cosmetics are cosmetics for frizzy hair and cosmetics for hair softening, they are superior to conventional cosmetics in terms of their frizzy hair correction effect and their hair softening effect.

When the cosmetics are pretreatment agents for hair dyeing, they are almost equivalent to conventional cosmetics in terms of hair damage and texture, and much improved in terms of their dyeing effect with acidic hair dyeing agents.

When the cosmetics are human hair remover they are superior to conventional cosmetics in terms of their odor and safety in hair removing effect.

What is claimed is:

1. A composition for treating human hair comprising a solution having a thiol compound of the formula:

$$HS-(CH_2)_n-NH-(CH_2)_m-NH_2$$

wherein n and m are integers from 1 to 4 or the salts of the formula, a solvent, a pH adjusting agent present in the composition in an amount to achieve a pH of between 3 to 11, and agent for reducing skin irritation, said thiol compound being present in the composition in an amount of between about 1.0 to 50 percent by weight, and a hair reductant present in the composition in an amount sufficient to achieve a weight ratio of said thiol compound to said hair reductant of between 0.05 to 100.

* * * * *